(12) United States Patent
Ohnishi et al.

(10) Patent No.: US 7,876,023 B2
(45) Date of Patent: Jan. 25, 2011

(54) PIEZOELECTRIC/ELECTROSTRICTIVE MEMBRANE SENSOR

(75) Inventors: Takao Ohnishi, Kiyosu (JP); Hideki Shimizu, Ohbu (JP); Takaaki Koizumi, Tajimi (JP)

(73) Assignee: NGK Insulators, Ltd., Nagoya (JP)

( * ) Notice: Subject to any disclaimer, the term of this patent is extended or adjusted under 35 U.S.C. 154(b) by 10 days.

(21) Appl. No.: 12/317,785

(22) Filed: Dec. 30, 2008

(65) Prior Publication Data

US 2009/0120183 A1 May 14, 2009

(30) Foreign Application Priority Data

| Jul. 4, 2006 | (JP) | ............................. 2006-184061 |
| Aug. 14, 2006 | (JP) | ............................. 2006-221129 |
| Oct. 31, 2006 | (JP) | ............................. 2006-295806 |
| Mar. 14, 2007 | (JP) | ............................. 2007-065922 |

(51) Int. Cl.
*H01L 41/04* (2006.01)
*H01L 41/08* (2006.01)

(52) U.S. Cl. ................... 310/324; 310/323.21
(58) Field of Classification Search ............... 310/324, 310/323.21
See application file for complete search history.

(56) References Cited

U.S. PATENT DOCUMENTS

| 5,281,888 | A | | 1/1994 | Takeuchi et al. |
| 5,376,857 | A | | 12/1994 | Takeuchi et al. |
| 5,825,119 | A | * | 10/1998 | Shibata et al. .............. 310/338 |
| 5,889,351 | A | * | 3/1999 | Okumura et al. ............ 310/321 |
| 6,360,606 | B2 | * | 3/2002 | Hirota et al. ................... 73/579 |
| 6,402,304 | B1 | * | 6/2002 | Qiu et al. ....................... 347/68 |
| 6,531,070 | B1 | | 3/2003 | Yamaguchi et al. |
| 6,774,541 | B1 | * | 8/2004 | Fukui ........................ 310/358 |
| 7,073,265 | B2 | * | 7/2006 | Senoo et al. ................... 30/364 |
| 7,332,851 | B2 | * | 2/2008 | Nanataki et al. ............. 310/358 |
| 7,667,377 | B2 | * | 2/2010 | Yamamoto et al. .......... 310/358 |
| 2007/0205700 | A1 | * | 9/2007 | Okamura et al. ............ 310/364 |
| 2007/0220724 | A1 | * | 9/2007 | Ohnishi et al. ............. 29/25.35 |
| 2007/0228894 | A1 | * | 10/2007 | Ishikura et al. ............. 310/363 |
| 2008/0072408 | A1 | * | 3/2008 | Sano et al. ................. 29/25.35 |
| 2009/0236945 | A1 | * | 9/2009 | Yamamoto et al. .......... 310/358 |

FOREIGN PATENT DOCUMENTS

| JP | 02-051023 | A1 | | 2/1990 |
| JP | 04262581 | A | * | 9/1992 |
| JP | 05-267742 | A1 | | 10/1993 |
| JP | 06-260694 | A1 | | 9/1994 |
| JP | 08-098884 | A1 | | 4/1996 |
| JP | 08-201265 | A1 | | 8/1996 |
| JP | 2001-146468 | A1 | | 5/2001 |
| JP | 2004-186436 | A1 | | 7/2004 |
| JP | 2005-014447 | A1 | | 1/2005 |
| JP | 2005-164495 | A1 | | 6/2005 |
| JP | 2005-191046 | A1 | | 7/2005 |
| JP | 2006-128357 | A1 | | 5/2006 |
| WO | WO 2007066453 | A1 | * | 6/2007 |

* cited by examiner

*Primary Examiner*—J. SanMartin
(74) *Attorney, Agent, or Firm*—Burr & Brown

(57) ABSTRACT

Disclosed is a piezoelectric/electrostrictive membrane sensor wherein the main component of terminal electrodes is contained in the vicinity of the surface of a piezoelectric/electrostrictive body. The membrane sensor is hardly electrostatically charged and thus prevented from electrostatic discharge damage and/or the attraction of dust, dirt or the like.

9 Claims, 3 Drawing Sheets
(1 of 3 Drawing Sheet(s) Filed in Color)

PIEZOELECTRIC/ELECTROSTRICTIVE MEMBRANE SENSOR

FIELD OF THE INVENTION

The present invention relates to a piezoelectric/electrostrictive membrane sensor which is hardly electrostatically charged.

BACKGROUND OF THE INVENTION

A piezoelectric/electrostrictive membrane sensor can be used for measuring fluid characteristics such as viscosity, density, and concentration by use of the electromechanical converting function of a piezoelectric/electrostrictive element in which a membranous piezoelectric/electrostrictive body disposed in the sensor is sandwiched between a pair of electrodes. When the piezoelectric/electrostrictive membrane sensor (the piezoelectric/electrostrictive element) is vibrated in a fluid, the sensor meets with a mechanical resistance caused by the viscosity resistance of the fluid, and the electric constant of the piezoelectric/electrostrictive element changes in a certain relation with respect to the mechanical resistance. Therefore, the sensor can detect the constant to measure the viscosity of the fluid.

It is to be noted that no prior document having the same object as or an object in common with the object of the present invention described below seems to be present, however examples of a prior document for reference of the piezoelectric/electrostrictive membrane sensor include Patent Documents 1 to 6.
  Patent Document 1: JP-A-8-201265
  Patent Document 2: JP-A-5-267742
  Patent Document 3: JP-A-6-260694
  Patent Document 4: JP-A-2005-164495
  Patent Document 5: JP-A-2-51023
  Patent Document 6: JP-A-8-98884

SUMMARY OF THE INVENTION

In the above piezoelectric/electrostrictive membrane sensor (also referred to simply as the sensor), in recent years, damage due to static electricity (electrostatic discharge damage) has raised a problem in the same manner as in other electronic components. All the substances have electrons in their atoms. It is considered that when bodies constituted of such substances, or a person and the body come in contact with (including friction, collision, and the like) or detach from each other, the electrons move, and an electrically unstable state is brought to generate this static electricity. When the static electricity is generated, with the movement of the electrons, the body or the person receiving the electrons forms a minus pole, and the body or the person discharging the electrons forms a plus pole.

In the case of the piezoelectric/electrostrictive membrane sensor, the piezoelectric/electrostrictive body as an insulator receives the electrons from another body, the person or air in the vicinity of the surface of the body, and can be brought into a charged state with the minus pole. Moreover, when the body discharges the electrons (discharges electricity) to the other body, the person or the air from this state, a voltage of several kVs is applied during the discharge, and the piezoelectric/electrostrictive body is sometimes damaged (the electrostatic discharge damage). Furthermore, when dust, dirt or the like charged with the plus pole is attracted to adhere to the vicinity of the surface of the piezoelectric/electrostrictive body in the charged state with the minus pole, a pair of electrodes sandwiching the piezoelectric/electrostrictive body therebetween thus causes short circuit, any desired voltage is not applied to the piezoelectric/electrostrictive body, the vibration of the sensor becomes unstable, and the characteristics of a fluid cannot be correctly measured.

The present invention has been developed in view of such a situation, and an object thereof is to provide a piezoelectric/electrostrictive membrane sensor which is hardly or minimally electrostatically charged, and thus prevented from the electrostatic discharge damage and attraction of dust, dirt or the like. As a result of investigations, it has been found that the above object can be achieved by the piezoelectric/electrostrictive membrane sensor in which a conductive material is appropriately present in the vicinity of the surface of a piezoelectric/electrostrictive body.

That is, according to the present invention, there is provided a piezoelectric/electrostrictive membrane sensor comprising: a ceramic substrate having a thin diaphragm portion and a thick portion integrally provided on the peripheral edge of the thin diaphragm portion, and including a cavity formed by the thin diaphragm portion and the thick portion so as to communicate with the outside; a piezoelectric/electrostrictive element having a laminate structure arranged on the outer surface of the thin diaphragm portion of the ceramic substrate and including a membranous piezoelectric/electrostrictive body, and a lower electrode and an upper electrode between which the piezoelectric/electrostrictive body is sandwiched; and terminal electrodes each of which connects the lower electrode or the upper electrode to a power source, the thin diaphragm portion of the ceramic substrate being configured to vibrate in conjunction with the driving of the piezoelectric/electrostrictive element, wherein a main component of the terminal electrodes is contained in the vicinity of the surface of the piezoelectric/electrostrictive body.

In the piezoelectric/electrostrictive membrane sensor according to the present invention, an auxiliary electrode may be provided so as to connect a terminal electrode (for the upper electrode) arranged on the ceramic substrate to the upper electrode formed on the piezoelectric/electrostrictive body. The lower electrode is arranged on the ceramic substrate, and is hence directly connected to a terminal electrode (for the lower electrode) similarly arranged on the ceramic substrate, and the auxiliary electrode is not necessary between the lower electrode and the terminal electrode (for the lower electrode). It is to be noted that in the present description, the vicinity of the surface of the piezoelectric/electrostrictive body is not the vicinity of the surface only, includes the surface and the vicinity of the surface, and indicates a portion in the vicinity of the surface, the portion including the surface.

In the piezoelectric/electrostrictive membrane sensor according to the present invention, the main component of the terminal electrodes contained in the vicinity of the surface of the piezoelectric/electrostrictive body is preferably diffused from the terminal electrodes to the vicinity of the surface of the piezoelectric/electrostrictive body by a heating treatment after the forming of the terminal electrodes.

In other words, the piezoelectric/electrostrictive membrane sensor according to the present invention can be obtained by forming the terminal electrodes, and then performing the heating treatment (the firing treatment) to diffuse (thermally diffuse) the main component of the conductive material constituting the terminal electrodes in the vicinity of the surface of the piezoelectric/electrostrictive body. Therefore, a remarkably small amount of the main component of the terminal electrodes is contained in the vicinity of the surface of the piezoelectric/electrostrictive body.

In the piezoelectric/electrostrictive membrane sensor according to the present invention, the terminal electrodes are preferably constituted of silver or a conductive material containing this metal as the main component. Silver may be contained in a metal state or a state of an oxide or a sulfide.

In the piezoelectric/electrostrictive membrane sensor according to the present invention, the upper electrode is preferably constituted of gold or a conductive material containing this metal as the main component. It is to be noted that the electrode simply mentioned in the present description indicates all of the terminal electrodes, the upper electrode, the lower electrode, and the auxiliary electrode (if any).

In the piezoelectric/electrostrictive membrane sensor according to the present invention, the piezoelectric/electrostrictive body preferably contains an alkali metal or an alkali earth metal. In this case, the piezoelectric/electrostrictive body is preferably constituted of $(Bi_{0.5}Na_{0.5})TiO_3$ or a piezoelectric/electrostrictive material containing this metal as the main component. That is, preferable examples of the alkali metal or the alkali earth metal include sodium.

In the piezoelectric/electrostrictive membrane sensor according to the present invention, the piezoelectric/electrostrictive body is preferably constituted of lead zirconate titanate or a piezoelectric/electrostrictive material containing this metal as the main component.

The piezoelectric/electrostrictive membrane sensor according to the present invention comprises the piezoelectric/electrostrictive element arranged on the thin diaphragm portion, and the thin diaphragm portion vibrates in conjunction with the driving of the piezoelectric/electrostrictive element, so that the sensor can be used as a heretofore known sensor for measuring fluid characteristics such as viscosity, density and concentration (see Patent Documents 1 to 6). When the piezoelectric/electrostrictive membrane sensor (the piezoelectric/electrostrictive element) is vibrated in a fluid, a mechanical resistance is received owing to the viscosity resistance of the fluid, and the electric constant of the piezoelectric/electrostrictive element changes in a constant relation with respect to the mechanical resistance, so that the electric constant can be detected to measure the viscosity of the fluid.

In addition, the piezoelectric/electrostrictive membrane sensor according to the present invention contains the main component of the terminal electrodes in the vicinity of the surface of the piezoelectric/electrostrictive body so that it is hardly electrostatically charged, and as such, the sensor is prevented from electrostatic discharge damage, while maintaining a high reliability of the sensor. Since the main component of the terminal electrodes is a conductive material, a portion containing the main component of the terminal electrodes in the vicinity of the surface of the piezoelectric/electrostrictive body is a low resistance portion. Even when the piezoelectric/electrostrictive body as an insulator receives electrons in the vicinity of the surface of the body, the electrons are immediately discharged via the low resistance portion. Therefore, the piezoelectric/electrostrictive membrane sensor according to the present invention is not easily brought into a state in which the sensor is electrostatically charged with the accumulated electrons. In consequence, in addition to the prevention of the electrostatic discharge damage, any dust, dirt or the like is not attracted to nor adheres to the vicinity of the surface, and as such, problems due to these causes are not easily generated. For example, any lowering of the precision of the sensor in the case where the upper electrode and the lower electrode sandwiching the piezoelectric/electrostrictive body therebetween causes a short circuit and any desired voltage cannot be applied to the piezoelectric/electrostrictive body, thereby causing the wrong detection of the sensor due to a mass of dust or the like being present.

As the heretofore known piezoelectric/electrostrictive membrane sensor, the sensor is not present in which the main component or the conductive material of the terminal electrodes is contained in the vicinity of the surface of the piezoelectric/electrostrictive body. Moreover, heretofore in the piezoelectric/electrostrictive membrane sensor, a technology has not been known in which the main component or the conductive material of the terminal electrodes is contained in the vicinity of the surface of the piezoelectric/electrostrictive body. Therefore, in the conventional piezoelectric/electrostrictive membrane sensor, the problem of the electrostatic discharge damage might constantly occur in the same manner as in another electronic component, but according to the piezoelectric/electrostrictive membrane sensor of the present invention, such a problem can be avoided.

In the preferable configuration of the piezoelectric/electrostrictive membrane sensor according to the present invention, the main component of the terminal electrodes contained in the vicinity of the surface of the piezoelectric/electrostrictive body is diffused from the terminal electrodes to the vicinity of the surface of the piezoelectric/electrostrictive body by the heating treatment after the forming of the terminal electrodes. Therefore, a remarkably small amount of the main component of the terminal electrodes is contained in the vicinity of the surface of the piezoelectric/electrostrictive body. Therefore, the sensor is hardly electrostatically charged. On the other hand, the main component of the terminal electrodes contained in the vicinity of the surface of the piezoelectric/electrostrictive body does not cause a short circuit between the upper electrode and the lower electrode, and the desired voltage can be applied to the piezoelectric/electrostrictive body. Therefore, the piezoelectric/electrostrictive element can be driven to vibrate the thin diaphragm portion in conjunction with the driving, and the sensor can exert excellent performance.

In the preferable configuration of the piezoelectric/electrostrictive membrane sensor according to the present invention, the terminal electrodes are constituted of silver as a low melting point material or the conductive material containing this component as the main component. The upper electrode is constituted of gold having a melting point higher than that of silver, or the conductive material containing this component as the main component. Therefore, only silver as the main component of the terminal electrodes is easily contained in the vicinity of the surface of the piezoelectric/electrostrictive body by diffusion accompanying the heating treatment. That is, it can be said that the preferable configuration of the piezoelectric/electrostrictive membrane sensor according to the present invention is easily manufactured.

In the preferable configuration of the piezoelectric/electrostrictive membrane sensor according to the present invention, the piezoelectric/electrostrictive body is constituted of lead zirconate titanate (PZT) having a large piezoelectric constant or the piezoelectric/electrostrictive material containing this component as the main component, or the body is similarly constituted of $(Bi_{0.5}Na_{0.5})TiO_3$ having a large piezoelectric constant or the piezoelectric/electrostrictive material containing this component as the main component, so that the sensor can realize a high output.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
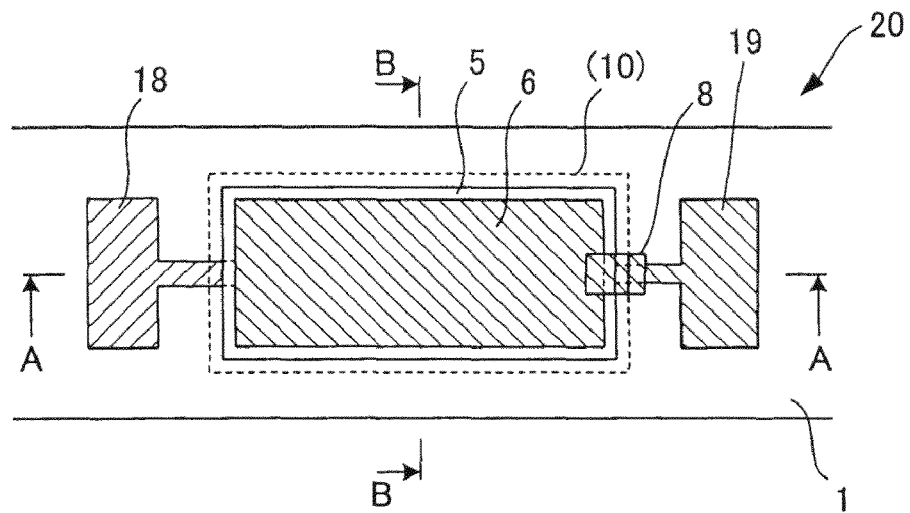
FIG. 1 is a plan view showing one embodiment of a piezoelectric/electrostrictive membrane sensor according to the present invention.

DESCRIPTION OF REFERENCE NUMERALS 1 ceramic substrate
2 thick portion
3 thin diaphragm portion
4 lower electrode
5 piezoelectric/electrostrictive body
6 upper electrode
7 joining layer
8 auxiliary electrode
9 through hole
10 cavity
12 piezoelectric/electrostrictive element
18 terminal electrode
19 terminal electrode
20 piezoelectric/electrostrictive membrane sensor

DETAILED DESCRIPTION OF THE INVENTION

Embodiments of the present invention will hereinafter be described appropriately with reference to the drawings, but the present invention is not limited to these embodiments, when interpreted. The present invention can variously be changed, modified, improved and replaced based on the knowledge of any person skilled in the art without departing from the scope of the present invention. For example, the drawings show the preferable embodiments of the present invention, but the present invention is not restricted by configuration or information shown in the drawings. To implement or verify the present invention, means similar or equivalent to that described in the present description is applicable, but preferable means is the following means.

Figure 2:
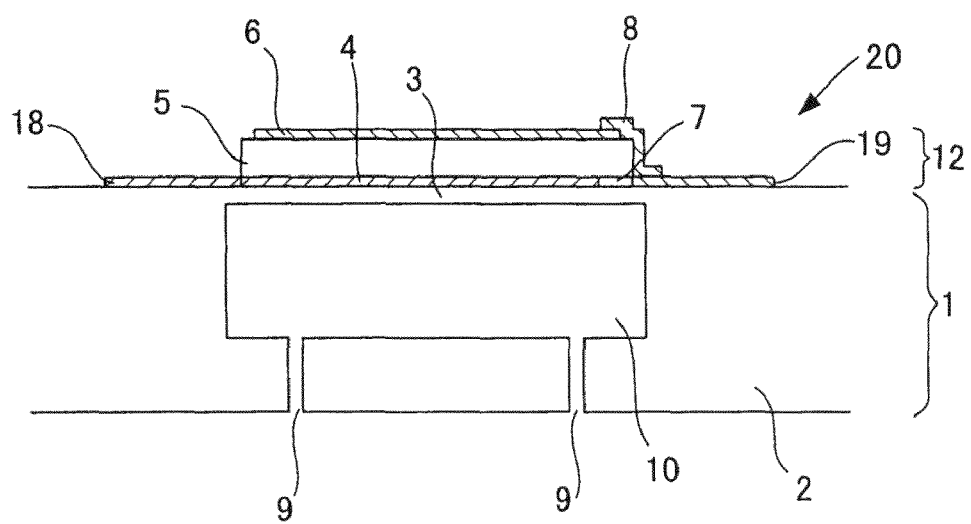
FIG. 2 is a sectional view showing a section cut along the line AA in FIG. 1.
Figure 3:
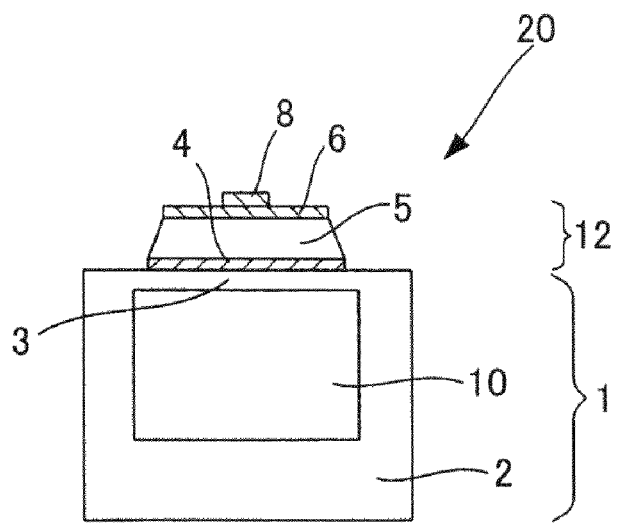
FIG. 3 is a sectional view showing a section cut along the line BB in FIG. 1.

First, the constitution of a piezoelectric/electrostrictive membrane sensor according to the present invention will be described. FIG. 1 is a plan view (a top view) showing one embodiment of the piezoelectric/electrostrictive membrane sensor according to the present invention, FIG. 2 is a sectional view showing a section cut along the line AA in FIG. 1, and FIG. 3 is a sectional view showing a section cut along the line BB in FIG. 1. A piezoelectric/electrostrictive membrane sensor 20 shown in FIGS. 1 to 3 includes a ceramic substrate 1 and a piezoelectric/electrostrictive element 12. The ceramic substrate 1 has a thin diaphragm portion 3 and a thick portion 2 integrally provided on the peripheral edge of the thin diaphragm portion 3, and the ceramic substrate 1 is provided with a cavity 10 formed by the thin diaphragm portion 3 and the thick portion 2 so as to communicate with the outside via through holes 9. The piezoelectric/electrostrictive element 12 is arranged on the outer surface of the thin diaphragm portion 3 of the ceramic substrate 1, and has a laminate structure formed by a membranous piezoelectric/electrostrictive body 5 and a pair of membranous electrodes (an upper electrode 6 and a lower electrode 4) sandwiching the piezoelectric/electrostrictive body 5 therebetween.

In the piezoelectric/electrostrictive membrane sensor 20, the lower electrode 4 formed on the thin diaphragm portion 3 of the ceramic substrate 1 on the underside of the piezoelectric/electrostrictive body 5 is directly and conductively connected to a terminal electrode 18 (for the lower electrode). The upper electrode 6 formed on the upside of the piezoelectric/electrostrictive body 5 is conductively connected to a terminal electrode 19 (for the upper electrode) via an auxiliary electrode 8. The terminal electrode 19 (for the upper electrode) is insulated from the lower electrode 4 by a joining layer 7 sandwiched between the electrodes. The joining layer 7 is formed so as to enter the underside of the piezoelectric/electrostrictive body 5, and is a layer having a function of connecting the piezoelectric/electrostrictive body 5 to the thin diaphragm portion 3. The piezoelectric/electrostrictive body 5 is formed in such a size as to cover the lower electrode 4, and the upper electrode 6 is formed so as to straddle the piezoelectric/electrostrictive body 5. In the vicinity of the exposed surface of the piezoelectric/electrostrictive body 5 which is not covered with the upper electrode 6 and the auxiliary electrode 8, a main component of the terminal electrodes 18, 19 described later is contained. It is to be noted that the joining layer 7 is appropriately applicable in accordance with the application of the sensor, and a joining layer 7 portion may be brought into an incompletely joined state.

In the piezoelectric/electrostrictive membrane sensor 20, when the piezoelectric/electrostrictive element 12 is driven (displacement is generated), the thin diaphragm portion 3 of the ceramic substrate 1 vibrates in conjunction with the driving. The thin diaphragm portion 3 of the ceramic substrate 1 usually has a thickness of 50 μm or less, preferably 30 μm or less, further preferably 15 μm or less so that the vibration of the piezoelectric/electrostrictive body 5 is not disturbed. As the planar shape of the thin diaphragm portion 3, any shape such as a rectangular shape, a square shape, a triangular shape, an elliptic shape or a perfectly circular shape may be employed, but the rectangular shape or the perfectly circular shape is selected if necessary, in the application of the sensor in which a resonance mode to be excited needs to be simplified.

Next, the material of each constitutional requirement of the piezoelectric/electrostrictive membrane sensor according to the present invention will be described in accordance with the piezoelectric/electrostrictive membrane sensor 20 as an example. The material for use in the ceramic substrate 1 is preferably a material having thermal resistance, chemical stability and insulation. This is because the lower electrode 4, the piezoelectric/electrostrictive body 5 and the upper electrode 6 are sometimes thermally treated when integrated. Moreover, when the piezoelectric/electrostrictive membrane sensor 20 detects the characteristics of a solution, the solution sometimes has conductivity or corrosive properties. Examples of a preferably usable material include stabilized zirconium oxide, partially stabilized zirconium oxide, aluminum oxide, magnesium oxide, mullite, aluminum nitride, silicon nitride and glass. Among these materials, stabilized zirconium oxide and partially stabilized zirconium oxide are most preferable, because the materials keep a high mechanical strength or have an excellent tenacity or the like even in a case where the thin diaphragm portion 3 is remarkably thinly formed.

As the material of the piezoelectric/electrostrictive body 5, any material may be used as long as the material exerts a piezoelectric/electrostrictive effect. Examples of a preferable material satisfying the conditions include lead zirconate titanate or a piezoelectric/electrostrictive material containing this component as a main component, $(Bi_{0.5}Na_{0.5})TiO_3$ or a material containing this component as the main component, or $(1-x)(Bi_{0.5}Na_{0.5})TiO_3$-$xKNbO_3$ (x is a molar fraction of $0 \leq x \leq 0.06$) or a material containing this component as the main component.

As the material of the joining layer 7, an organic or inorganic material having close contact properties and joining properties with respect to both the piezoelectric/electrostrictive body 5 and the ceramic substrate 1 may be used. The material for use preferably has a thermal expansion coefficient having an intermediate value between the thermal expansion coefficient of the material of the ceramic substrate 1 and the thermal expansion coefficient of the material for use in the piezoelectric/electrostrictive body 5 in order to obtain highly reliable joining properties. When the piezoelectric/electrostrictive body 5 is thermally treated, a glass material having a softening point higher than the thermal treatment temperature of the piezoelectric/electrostrictive body 5 is preferably used. The piezoelectric/electrostrictive body 5 is firmly joined to the ceramic substrate 1, and deformation by the thermal treatment is suppressed owing to the high softening point. Furthermore, when the piezoelectric/electrostrictive body 5 is constituted of $(Bi_{0.5}Na_{0.5})TiO_3$ or the material containing this component as the main component, or $(1-x)(Bi_{0.5}Na_{0.5})TiO_3$-$xKNbO_3$ (x is the molar fraction of $0 \leq x \leq 0.06$) or the material containing this component as the main component, as the material of the joining layer 7, a material containing $(1-x)(Bi_{0.5}Na_{0.5})TiO_3$-$xKNbO_3$ (x is a molar fraction of $0.08 \leq x \leq 0.5$) as the main component is preferably employed. This is because the material has high close contact properties with respect to both the piezoelectric/electrostrictive body 5 and the ceramic substrate 1, and the piezoelectric/electrostrictive body 5 and the ceramic substrate 1 can be prevented from adverse affect during the thermal treatment. That is, since the material has a component similar to that of the piezoelectric/electrostrictive body 5, the material has high close contact properties with respect to the piezoelectric/electrostrictive body 5. Moreover, there is hardly problem due to the diffusion of a heterologous element which might be generated in a case where glass is used. Furthermore, since much $KNbO_3$ is contained, the material has a high reactivity with the ceramic substrate 1, and firm joining is possible. In addition, $(1-x)(Bi_{0.5}Na_{0.5})TiO_3$-$xKNbO_3$ (x is the molar fraction of $0.08 \leq x \leq 0.5$) hardly exerts piezoelectric/electrostrictive characteristics. Therefore, during use, any displacement is not generated with respect to an electric field generated in the lower electrode 4 and the auxiliary electrode 8, and hence stable sensor characteristics can be obtained.

As to the materials of the electrodes, the terminal electrodes employ silver or a conductive material containing this component as the main component, the auxiliary electrode and the upper electrode employ gold or a conductive material containing this component as the main component, and the lower electrode employs platinum or a conductive material containing this component as the main component.

Next, a manufacturing method of the piezoelectric/electrostrictive membrane sensor according to the present invention will be described in accordance with the manufacturing of the piezoelectric/electrostrictive membrane sensor 20 as an example.

(Step 1. Preparation of Ceramic Substrate) The ceramic substrate 1 can be prepared by a green sheet laminating process. Specifically, the predetermined number of ceramic green sheets constituted of the above-mentioned ceramic material as the main component are prepared. A hole portion having a predetermined shape constituting the cavity 10 after the lamination is made in the necessary number of the resultant ceramic green sheets by use of a punch processor including a punch and a die, and hole portions having a predetermined shape forming the through holes 9 after the lamination are made in the necessary number of the other sheets. Then, the ceramic green sheet constituting the thin diaphragm portion 3 later, the ceramic green sheet having the hole portion made so as to constitute the cavity 10, and the ceramic green sheet having the hole portion made so as to constitute the through holes 9 are laminated in this order to obtain a laminated green body, and the body is fired to obtain the ceramic substrate 1. One ceramic green sheet has a thickness of about 100 to 300 μm excluding the ceramic green sheet constituting the thin diaphragm portion 3.

The ceramic green sheet can be prepared by a heretofore known ceramic manufacturing method. One example will be described. Desired ceramic material powder is prepared, and blended with a binder, a solvent, a dispersant, a plasticizer or the like in a desired composition to prepare a slurry, and this slurry is subjected to a defoaming treatment and a sheet forming process such as a doctor blade process, a reverse roll coater process or a reverse doctor roll coater process, whereby the ceramic green sheet can be obtained.

(Step 2. Formation of Lower Electrode) After forming a membrane by any known membrane forming technique, the formed membrane is dried and fired to form the membranous lower electrode 4 on the outer surface of the thin diaphragm portion 3 of the ceramic substrate 1. Specifically, as the membrane forming technique, a thin membrane forming technique such as ion beam, sputtering, vacuum deposition, CVD, ion plating or plating or a thick membrane forming technique such as screen printing, spray or dipping is appropriately selected. In particular, the sputtering process or the screen printing process is preferably selected. The membrane is dried at 50 to 150° C., and fired at 1100 to 1300° C. Firing time is about one to two hours.

(Step 3. Formation of Joining Layer) To form the joining layer 7, a usual thick membrane technique is used. In particular, a stamping process or the screen printing process is preferably used. Moreover, when a portion to be formed has a size of about several ten μms to several hundred μms, an ink jet process is preferably used. When the joining layer 7 needs to be thermally treated, the layer may thermally be treated before forming the next piezoelectric/electrostrictive body 5, after forming the piezoelectric/electrostrictive body 5 or simultaneously with the forming.

(Step 4. Formation of Piezoelectric/Electrostrictive Body) To form the membranous piezoelectric/electrostrictive body 5, a membrane is formed by a known any membrane forming process, and fired in the same manner as in the lower electrode 4. From a viewpoint of cost reduction, as a membrane forming technique, the screen printing is preferably used. The membrane has a thickness of preferably 100 μm or less, further preferably 50 μm or less for increasing displacement (i.e., improving characteristics), more preferably 5 to 20 μm. The thus formed piezoelectric/electrostrictive body 5 is integrated with the beforehand formed lower electrode 4 and joining layer 7 during the firing. Firing temperature is in a range of about 900 to 1400° C., and firing time is in a range of about two to 50 hours. The membrane is preferably fired while controlling the atmosphere together with an evaporation source of the piezoelectric/electrostrictive material so that the piezoelectric/electrostrictive body 5 does not become unstable at a high temperature.

(Step 5. Formation of Terminal Electrodes) To form the terminal electrode 19 for the upper electrode 6 and the terminal electrode 18 for the lower electrode 4, membranes are formed by a membrane forming process similar to that of the lower electrode 4, dried and fired. During the firing, the terminal electrode 18 is joined to the lower electrode 4 and the piezoelectric/electrostrictive body 5 to form an integral structure.

(Step 6. Formation of Upper Electrode) To form the upper electrode 6, a membrane is formed by a membrane forming process similar to that of the lower electrode 4, dried and fired. The membrane is fired at 500 to 900° C., and firing time is in a range of about one to two hours.

Figure 4:
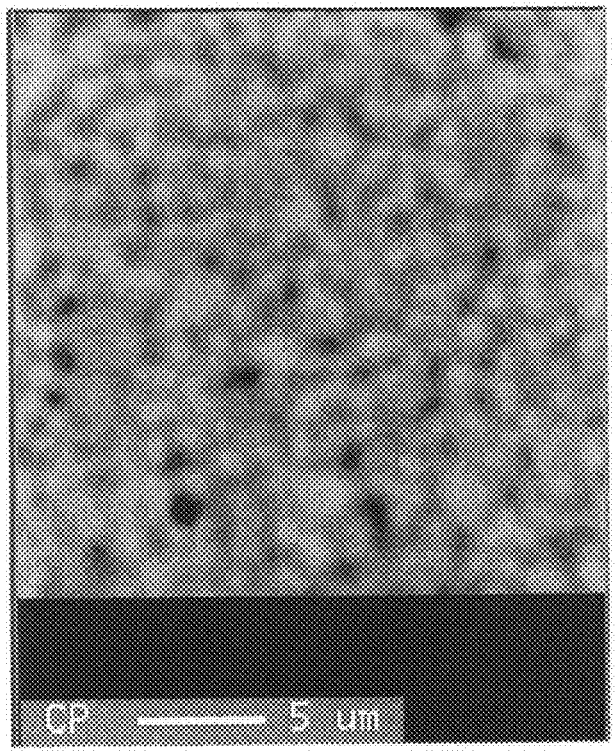
FIG. 4 is a diagram showing one embodiment of the piezoelectric/electrostrictive membrane sensor according to the present invention, and is a photograph showing the surface of a piezoelectric/electrostrictive body by a scanning electron microscope.
Figure 5:
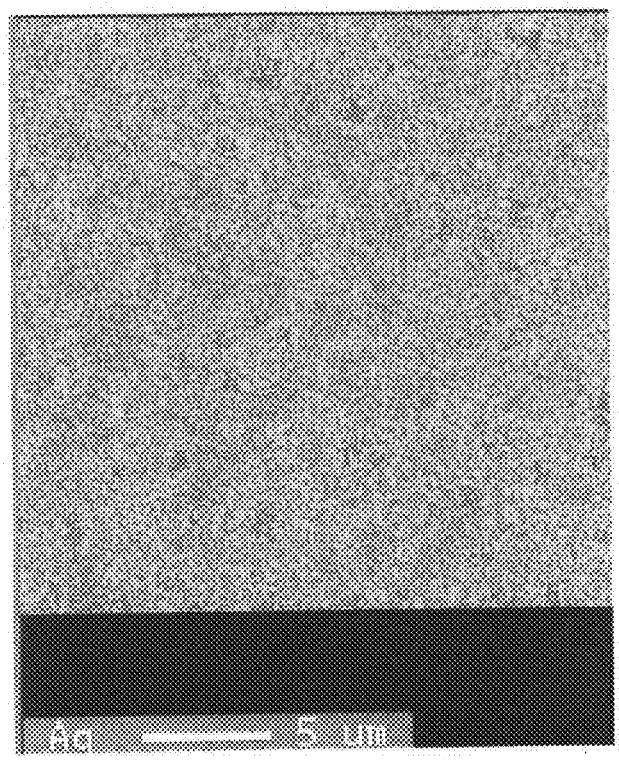
FIG. 5 is a diagram showing one embodiment of the piezoelectric/electrostrictive membrane sensor according to the present invention, and is a photograph showing the surface of the piezoelectric/electrostrictive body by an X-ray micro analyzer (EPMA, Electron Probe Micro Analyzer) and showing a behavior that silver as the material of terminal electrodes is diffused in the piezoelectric/electrostrictive body.

In this step of forming the upper electrode, the main component (silver) of the beforehand formed terminal electrodes 18, 19 is thermally diffused, and contained in the vicinity of the surface of the beforehand formed piezoelectric/electrostrictive body 5. That is, the resultant piezoelectric/electrostrictive membrane sensor 20 is the piezoelectric/electrostrictive membrane sensor according to the present invention. FIGS. 4 and 5 are diagrams showing one embodiment of the piezoelectric/electrostrictive membrane sensor according to the present invention. FIG. 4 is a photograph showing the surface of the piezoelectric/electrostrictive body by a scanning electron microscope. Moreover, FIG. 5 is a photograph showing the surface of the piezoelectric/electrostrictive body by an X-ray micro analyzer (EPMA, Electron Probe Micro Analyzer) and showing a behavior that silver as the material of the terminal electrodes is diffused in the piezoelectric/electrostrictive body. It is to be noted that the photograph of the EPMA shows that a target substance gradually increases (is present) in order of blue, green, yellow, vermillion and red (blue shows the smallest amount, and red shows the largest amount). After forming (including firing) the terminal electrodes, the upper electrode is formed (including the firing), so that as shown in FIG. 5, silver as the material of the terminal electrodes 18, 19 can be contained in the vicinity of the surface of the piezoelectric/electrostrictive body 5. Silver is preferably present in a pole surface layer in a thickness direction, and silver can be present in the vicinity of the surface of the piezoelectric/electrostrictive body 5 by sputtering or the like. However, silver is preferably thermally diffused in that silver can more thinly, easily and uniformly be diffused in the pole surface layer and in that resistance can slightly be lowered while keeping insulation. It is to be noted that in an example in which the membrane thickness of the piezoelectric/electrostrictive body 5 was set to 5 to 20 μm, it has been confirmed that silver was diffused in a state in which the membrane thickness was 20 μm or less and that satisfactory characteristics were obtained.

Moreover, the firing temperature can be adjusted or the content of the main component (silver) included in a material for use in forming the terminal electrodes 18, 19 can be adjusted to adjust the amount of the main component (silver) of the terminal electrodes 18, 19 contained in the vicinity of the surface of the piezoelectric/electrostrictive body 5 of the resultant piezoelectric/electrostrictive membrane sensor 20.

(Step 7. Formation of Auxiliary Electrode) To form the auxiliary electrode 8, a membrane is formed by a membrane forming process similar to that of the upper electrode 6, dried and fired. During the firing, the auxiliary electrode 8 is joined to the upper electrode 6, the piezoelectric/electrostrictive body 5 and the terminal electrode 19 to form an integral structure.

The piezoelectric/electrostrictive element 12 is obtained as described above, but the piezoelectric/electrostrictive element 12 only may be separately prepared, and attached to the ceramic substrate 1 or directly formed on the ceramic substrate 1.

It is to be noted that as long as the firing is performed in the step of forming the terminal electrodes 18, 19 and the firing is performed in the step of forming the upper electrode 6, to form the lower electrode 4, the joining layer 7, the piezoelectric/electrostrictive body 5 and the terminal electrodes 18, 19, instead of the firing (the thermal treatment) of each formed membrane described above, the membranes may be successively formed and collectively and simultaneously fired (thermally treated). Similarly, to form the upper electrode 6 and the auxiliary electrode 8, instead of the firing (the thermal treatment) of each formed membrane, the membranes may be successively formed and collectively and simultaneously fired (thermally treated). In this case, to realize satisfactory joining properties, needless to say, the temperature is appropriately selected.

In the above steps, the piezoelectric/electrostrictive membrane sensor 20 including the ceramic substrate 1 and the piezoelectric/electrostrictive element 12 is structurally completed.

(Step 8. Polarization) A direct-current high voltage (for example, a voltage of DC 300 V) is applied across the upper electrode 6 and the lower electrode 4 in the piezoelectric/electrostrictive element 12 of the piezoelectric/electrostrictive membrane sensor 20 to perform a polarization treatment.

(Step 9. Displacement Measurement) An alternate-current sine wave voltage of 0 to 200 V, 1 kHz is applied, and the displacement of the piezoelectric/electrostrictive element 12 of the piezoelectric/electrostrictive membrane sensor 20 subjected to the polarization treatment is measured using a laser Doppler vibration meter.

(Step 10. UV Sheet Attachment) A large number of piezoelectric/electrostrictive membrane sensors 20 are usually manufactured at once. In this case, a UV sheet is attached as fixing means to the surface of the piezoelectric/electrostrictive membrane sensor 20 on a side opposite to the piezoelectric/electrostrictive element 12, and fixed to a predetermined position.

(Step 11. Outer Shape Cutting) When a large number of sensors are formed, the prior steps are performed without performing cutting, but here the cutting is performed using a dicer to obtain the individual piezoelectric/electrostrictive membrane sensors 20.

(Step 12. Sorting) To select satisfactory bodies, bodies having a displacement of a reference value or less in Step 9 are deleted as defective bodies.

(Step 13. Heating Treatment) The outer shape cutting is usually performed while performing washing with water. Therefore, to remove moisture, the satisfactory bodies are subjected to a heating treatment, and dried. Temperature conditions are in a range of 60° C. or more and 900° C. or less. Even by temperature adjustment in this step, the amount of the main component (silver) of the terminal electrodes 18, 19 contained in the vicinity of the surface of the piezoelectric/electrostrictive body 5 of the resultant piezoelectric/electrostrictive membrane sensor 20 can be adjusted.

(Step 14. Appearance Inspection) Finally, appearance is inspected, and then the sensors are shipped.

Next, the application of the piezoelectric/electrostrictive membrane sensor according to the present invention will be described. The piezoelectric/electrostrictive membrane sensor according to the present invention is usable as a sensor constituting a fluid characteristic measurement apparatus. The fluid characteristic measurement apparatus may be constituted of the piezoelectric/electrostrictive membrane sensor according to the present invention, a power source for applying a voltage across the upper electrode and the lower electrode to drive the piezoelectric/electrostrictive element of this piezoelectric/electrostrictive membrane sensor, and electric constant monitoring device for detecting the change of an electric constant accompanying the vibration of the thin diaphragm portion of the piezoelectric/electrostrictive membrane sensor.

The fluid characteristic measurement apparatus is an apparatus capable of measuring the characteristics of a fluid by the detection of the electric constant by the electric constant monitoring device. In the fluid, when the piezoelectric/electrostrictive element is driven in the piezoelectric/electrostrictive membrane sensor to vibrate the thin diaphragm portion, mechanical resistance is received owing to the viscosity resistance of the fluid, and the electric constant of the piezoelectric/electrostrictive element changes in a constant relation with respect to the mechanical resistance. Therefore, the change can be detected to measure the viscosity of the fluid.

In the basic principle of this fluid characteristic measurement apparatus in measuring the characteristics of the fluid, there is used correlation between the amplitudes of the piezoelectric/electrostrictive element and the thin diaphragm portion as vibrators and the characteristics of the fluid which comes in contact with the vibrators. In a case where the fluid has the characteristics of the viscosity resistance, when the fluid has a large viscosity resistance, the amplitudes of the vibrators decrease. When the viscosity resistance decreases, the amplitudes of the vibrators increase. Moreover, a vibration configuration in a mechanical system such as the vibration of the vibrators can be replaced with an equivalent circuit of an electric system. In this case, it may be supposed that the amplitude corresponds to current. Moreover, the vibration state of the equivalent circuit indicates the changes of various electric constants near a resonance point. Among electric constants such as loss coefficient, phase, resistance, reactance, conductance, susceptance, inductance, and capacitance, the loss coefficient or the phase having the maximum or minimum change point of the change near the resonance frequency of the equivalent circuit is preferably used as an index. The detection of the loss coefficient or the phase can more easily be performed as compared with the other electric constants.

It is to be noted that even in a case where the fluid has characteristics other than the viscosity resistance (for example, the pressure of the fluid (needless to say, the presence of the fluid)), when an element influencing the vibration of the vibrators is present in the fluid having the characteristics to be measured, the characteristics may be associated with the changes of the vibrations of the piezoelectric/electrostrictive element and the thin diaphragm portion to measure the characteristics. When the fluid is a solution and the concentration of the solution changes to change viscosity and density, the vibration configurations of the piezoelectric/electrostrictive element and the thin diaphragm portion in the solution change, so that the concentration of the solution can be measured. That is, the fluid characteristic measurement apparatus according to the present invention can measure the viscosity, density and concentration of the solution.

The piezoelectric/electrostrictive membrane sensor according to the present invention can measure the characteristics of the fluid, which can be used to judge the flow state of the fluid or judge whether or not the fluid is present. When, for example, any fluid as a measurement target is not present, the amplitude changes of the vibrators (the piezoelectric/electrostrictive element and the thin diaphragm portion) become remarkable, and the changes are easily detected. Specifically, the piezoelectric/electrostrictive membrane sensor according to the present invention includes the monitoring of the dropping state of a medical dripping apparatus, and the sensor can preferably be used as a measuring instrument sensor for monitoring the feed or infusion state of any solution, that is, whether or not the solution flows (as planned) (for a conventional technology concerning the dripping, refer to Patent Documents 5 and 6).

In the dripping apparatus including a bottle containing a drug solution, a tube, a drip chamber through which the dripping of the drug solution can visually be checked, and an injection needle, the piezoelectric/electrostrictive membrane sensor according to the present invention is attached to one of the bottle, the tube and the drip chamber (several positions, if necessary). The apparatus further includes a control monitoring apparatus in which information on the flow state of the fluid or the presence of the fluid (the change of the electric constant) detected in this manner is input to perform computation, display, communication and the like, so that a dripping management apparatus can be constructed. The computation includes the predicting of a dripping end time based on a timer disposed in the control monitoring apparatus, the detection of an abnormality with the elapse of predetermined time and the like. A display target includes data such as a flow rate, and a warning. The communication includes the outputting to a nurse station. This dripping management apparatus can be applied to the medical dripping apparatus to ease patients and decrease burdens on nurses.

INDUSTRIAL APPLICABILITY

A piezoelectric/electrostrictive membrane sensor according to the present invention can be used as a sensor for measuring the characteristics of a fluid. Specifically, the sensor can be used as a sensor for each measuring instrument of viscosity, density or concentration. In addition, the sensor can preferably be used as a sensor of a measuring instrument which includes the monitoring of the dripping state of a medical dripping apparatus and which monitors the feed or infusion state of any solution.

The invention claimed is;

1. A piezoelectric/electrostrictive membrane sensor comprising:
    a ceramic substrate having a thin diaphragm portion and a thick portion integrally provided on the peripheral edge of the thin diaphragm portion, and including a cavity formed by the thin diaphragm portion and the thick portion so as to communicate with the outside;
    a piezoelectric/electrostrictive element having a laminate structure arranged on the outer surface of the thin diaphragm portion of the ceramic substrate and including a membranous piezoelectric/electrostrictive body, and a lower electrode and an upper electrode between which the piezoelectric/electrostrictive body is sandwiched; and
    terminal electrodes each of which connects the lower electrode or the upper electrode to a power source,
    the thin diaphragm portion of the ceramic substrate being configured to vibrate in conjunction with the driving of the piezoelectric/electrostrictive element, wherein a main component of the terminal electrodes is contained in the vicinity of the exposed surface of the piezoelectric/electrostrictive body that is not covered by the electrodes.

2. The piezoelectric/electrostrictive membrane sensor according to claim 1, wherein the main component of the terminal electrodes contained in the vicinity of the surface of the piezoelectric/electrostrictive body is diffused from the terminal electrodes to the vicinity of the surface of the piezoelectric/electrostrictive body by a heating treatment after the forming of the terminal electrodes.

3. The piezoelectric/electrostrictive membrane sensor according to claim 2, wherein the terminal electrodes are constituted of silver or a conductive material containing this metal as the main component.

4. The piezoelectric/electrostrictive membrane sensor according to claim 1, wherein the terminal electrodes are constituted of silver or a conductive material containing this metal as the main component.

5. The piezoelectric/electrostrictive membrane sensor according to claim 1, wherein the upper electrode is constituted of gold or a conductive material containing this metal as the main component.

6. The piezoelectric/electrostrictive membrane sensor according to claim 1, wherein the piezoelectric/electrostrictive body contains an alkali metal or an alkali earth metal.

7. The piezoelectric/electrostrictive membrane sensor according to claim 6, wherein the piezoelectric/electrostrictive body is constituted of $(Bi_{0.5}Na_{0.5})TiO_3$ or a piezoelectric/electrostrictive material containing this metal as the main component.

8. The piezoelectric/electrostrictive membrane sensor according to claim 1, wherein the piezoelectric/electrostrictive body is constituted of lead zirconate titanate or a piezoelectric/electrostrictive material containing this metal as the main component.

9. The piezoelectric/electrostrictive membrane sensor according to claim 1, wherein the material composition of the terminal electrode is different from the material composition of the upper electrode, and wherein the material composition of the terminal electrode is different from the material composition of the lower electrode.

* * * * *

UNITED STATES PATENT AND TRADEMARK OFFICE
CERTIFICATE OF CORRECTION

PATENT NO. : 7,876,023 B2
APPLICATION NO. : 12/317785
DATED : January 25, 2011
INVENTOR(S) : Takao Ohnishi, Hideki Shimizu and Takaaki Koizumi It is certified that error appears in the above-identified patent and that said Letters Patent is hereby corrected as shown below:

Title Page

*please add*: Item (63), Related U.S. Application Priority Data

This application is a Continuation of PCT/JP2007/063765, filed July 4, 2007

Signed and Sealed this
Eighth Day of March, 2011

David J. Kappos
*Director of the United States Patent and Trademark Office*